United States Patent
Murakami et al.

(10) Patent No.: US 11,399,801 B2
(45) Date of Patent: Aug. 2, 2022

(54) MEDICAL DIAGNOSTIC-IMAGING APPARATUS AND MEDICAL-IMAGE PROCESSING APPARATUS

(71) Applicant: CANON MEDICAL SYSTEMS CORPORATION, Otawara (JP)

(72) Inventors: Yuri Murakami, Nasushiobara (JP); Takuya Sakaguchi, Utsunomiya (JP); Kazumasa Arakita, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 697 days.

(21) Appl. No.: 16/197,817

(22) Filed: Nov. 21, 2018

(65) Prior Publication Data

US 2019/0159759 A1     May 30, 2019

(30) Foreign Application Priority Data

Nov. 24, 2017  (JP) .............................. JP2017-225953
Nov. 1, 2018   (JP) .............................. JP2018-206363

(51) Int. Cl.
| | |
|---|---|
| *A61B 8/12* | (2006.01) |
| *A61B 8/00* | (2006.01) |
| *A61B 8/08* | (2006.01) |

(52) U.S. Cl.
CPC .......... *A61B 8/4466* (2013.01); *A61B 8/0883* (2013.01); *A61B 8/12* (2013.01); *A61B 8/483* (2013.01); *A61B 8/466* (2013.01); *A61B 8/523* (2013.01)

(58) Field of Classification Search
CPC ....... A61B 8/4466; A61B 8/12; A61B 8/0883; A61B 8/483; A61B 8/466; A61B 8/523; A61B 8/469; A61B 8/58; A61B 8/585; A61B 8/5261
See application file for complete search history.

(56) References Cited

U.S. PATENT DOCUMENTS

| | | | | |
|---|---|---|---|---|
| 2007/0167801 | A1* | 7/2007 | Webler ................... | A61B 8/445 600/459 |
| 2008/0177183 | A1* | 7/2008 | Courtney ............. | A61B 5/0084 600/463 |
| 2016/0095573 | A1* | 4/2016 | Tanaka ................... | A61B 8/461 600/443 |

FOREIGN PATENT DOCUMENTS

| | | | | |
|---|---|---|---|---|
| EP | 0626152 A1 | * | 11/1994 | ............. A61B 8/445 |
| JP | 2015-132 A | | 1/2015 | |
| JP | 2020028718 A | * | 2/2020 | ............... A61B 8/12 |

* cited by examiner

*Primary Examiner* — Catherine B Kuhlman
*Assistant Examiner* — Nicholas A Robinson
(74) *Attorney, Agent, or Firm* — Oblon, McClelland, Maier & Neustadt, L.L.P.

(57) ABSTRACT

A medical diagnostic-imaging apparatus according to an embodiment includes processing circuitry. The processing circuitry acquires three-dimensional medical image data in which a subject is imaged. The processing circuitry extracts a movable range of a probe based on a structure of the subject shown in the three-dimensional medical image data. The processing circuitry sets a target scan region to be a subject to scanning by the probe based on the extracted movable range. The processing circuitry displays the target scan region in the three-dimensional medical image data.

13 Claims, 8 Drawing Sheets

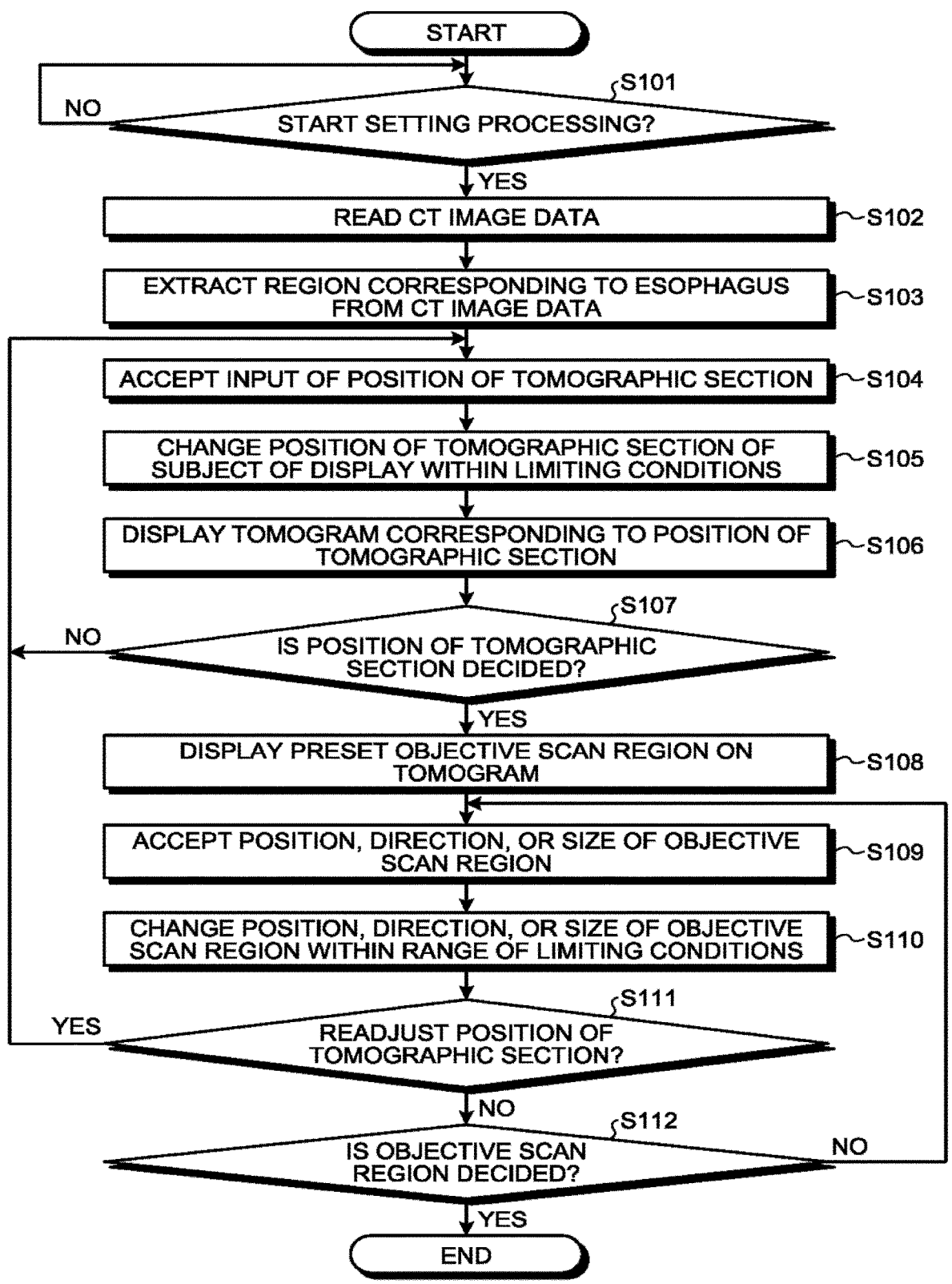

MEDICAL DIAGNOSTIC-IMAGING APPARATUS AND MEDICAL-IMAGE PROCESSING APPARATUS

CROSS-REFERENCE TO RELATED APPLICATIONS

This application is based upon and claims the benefit of priority from Japanese Patent Application No. 2017-225953, filed on Nov. 24, 2017; and Japanese Patent Application No. 2018-206363, filed on Nov. 1, 2018, the entire contents of all of which are incorporated herein by reference.

FIELD

Embodiments described herein relate generally to a medical diagnostic-imaging apparatus and a medical-image processing apparatus.

BACKGROUND

In heart valve treatment, an ultrasonic diagnostic apparatus and an X-ray computed tomography (CT) apparatus have conventionally been used in combination. For example, a doctor uses a CT image data that has been acquired by an X-ray CT apparatus before the operation to create a treatment plan while referring to desired multiplanar reconstruction (MPR) images. During the operation, a doctor give treatment, referring to the treatment plan created prior to the operation and real-time ultrasound images that are acquired by an ultrasonic diagnostic apparatus. It is preferable that a scan region (scanning section) of ultrasonic images to be displayed at this time be the same cross section as that of the MPR images referred in the treatment planning.

When imaging a heart valve by an ultrasonic diagnostic apparatus, a transesophageal echocardiography (TEE) probe can be used. The TEE probe is an ultrasound probe to be inserted from the mouth to an upper digestive canal, such as the esophagus and the stomach, to image a heart and the like by ultrasound. However, it is difficult to scan a desired area by using the TEE probe.

BRIEF DESCRIPTION OF THE DRAWINGS

FIG. 3 is a flowchart showing a procedure of setting processing in the ultrasonic diagnostic apparatus according to the first embodiment;

DETAILED DESCRIPTION

Figure 1:
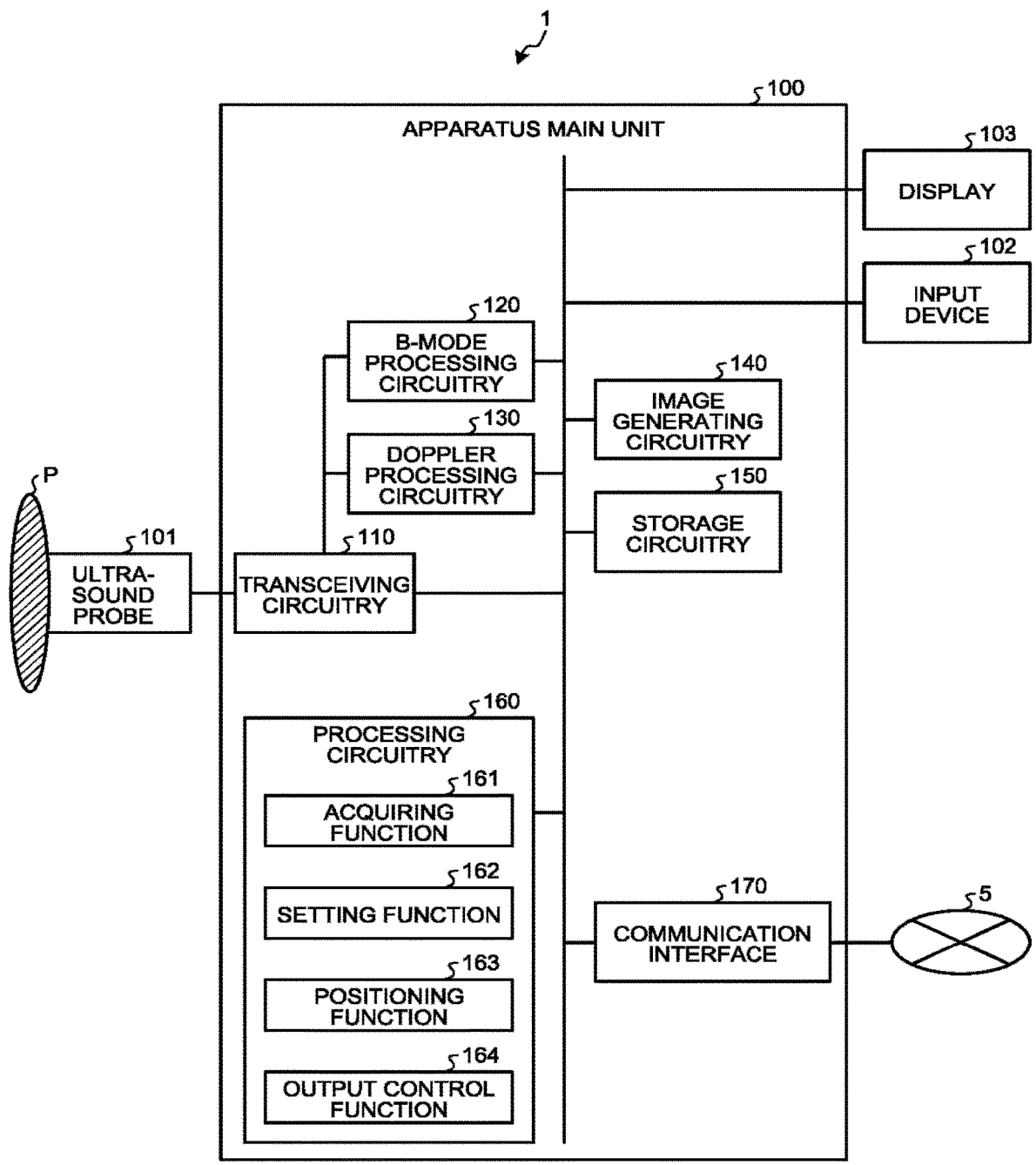
FIG. 1 is a block diagram showing a configuration example of an ultrasonic diagnostic apparatus according to a first embodiment.

An object of the present embodiment is to provide a medical diagnostic-imaging apparatus and a medical-image processing apparatus in which a desirable scan region can be easily set.

A medical diagnostic-imaging apparatus according to an embodiment includes processing circuitry. The processing circuitry acquires three-dimensional medical image data in which a subject is imaged. The processing circuitry extracts a movable range of a probe based on a structure of the subject shown in the three-dimensional medical image data. The processing circuitry sets a target scan region to be a subject to scanning by the probe based on the extracted movable range. The processing circuitry displays the target scan region in the three-dimensional medical image data.

The medical diagnostic-imaging apparatus and the medical-image processing apparatus according to the embodiment are explained below, referring to the drawings. The embodiment explained below is one example, and the medical diagnostic-imaging apparatus and the medical-image processing apparatus according to the embodiment are not limited to the explanation below.

First Embodiment

A configuration example of an ultrasonic diagnostic apparatus 1 according to a first embodiment is explained, using FIG. 1. FIG. 1 is a block diagram showing a configuration example of the ultrasonic diagnostic apparatus 1 according to the first embodiment. As shown in FIG. 1, the ultrasonic diagnostic apparatus 1 according to the first embodiment includes an apparatus main unit 100, an ultrasound probe 101, an input device 102, and a display 103. The ultrasound probe 101, the input device 102, and the display 103 are communicably connected to the apparatus main unit 100.

The ultrasound probe 101 has multiple piezoelectric transducers, and these piezoelectric transducers generate ultrasonic waves based on a driving signal provided by transceiving circuitry 110 included in the apparatus main unit 100. Moreover, the ultrasound probe 101 receives a reflected wave from the subject P and converts it into an electrical signal. The ultrasound probe 101 further includes a matching layer that is provided for the piezoelectric transducers, a backing material to prevent transmission of ultrasonic waves to the backward direction from the piezoelectric transducers, and the like. The ultrasound probe 101 is detachably connected to the apparatus main unit 100.

When ultrasonic waves are transmitted from the ultrasound probe 101 to the subject P, the transmitted ultrasonic waves are sequentially reflected by discontinuous surfaces of acoustic impedance in a body tissue of the subject P, and received by the piezoelectric transducers in the ultrasound probe 101 as a reflected-wave signal. The amplitude of the received reflected-wave signal is dependent on differences in the acoustic impedance on the discontinuous surface by which the ultrasonic waves are reflected. Reflected-wave signals when transmitted ultrasonic wave pulses are reflected by a surface of a moving blood flow, a cardiac wall, and the like are subjected to frequency deviation dependent on a velocity component of a moving body relative to a direction of transmission of ultrasonic waves by the Doppler effect.

The ultrasound probe 101 according to the first embodiment is, for example, a transesophageal echocardiography (TEE) probe capable of collecting volume data. The TEE probe is the ultrasound probe 101 that is inserted to an upper digestive canal, such as esophagus and stomach, to image a heart and the like by ultrasound. As one example, the ultrasound probe 101 is a three-dimensional (3D) TEE probe that has a two-dimensional array in which multiple transducers are arranged in a lattice shape. The TEE probe that has the two-dimensional array can rotate and swing a transducer surface that scans a section (plane) by electronic control. Moreover, for example, the TEE probe that has the two-dimensional array can collect volume data by rotating the scanning plane by 180°. The TEE probe is also known as transesophageal probe.

Figure 2A:
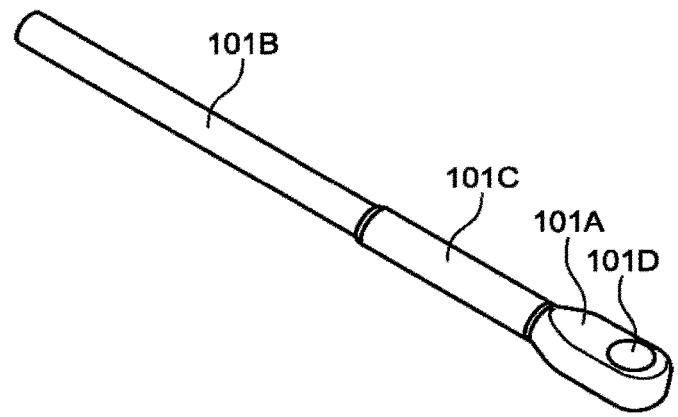
FIG. 2A is a diagram showing one example of a structure of an ultrasound probe according to the first embodiment.
Figure 2B:
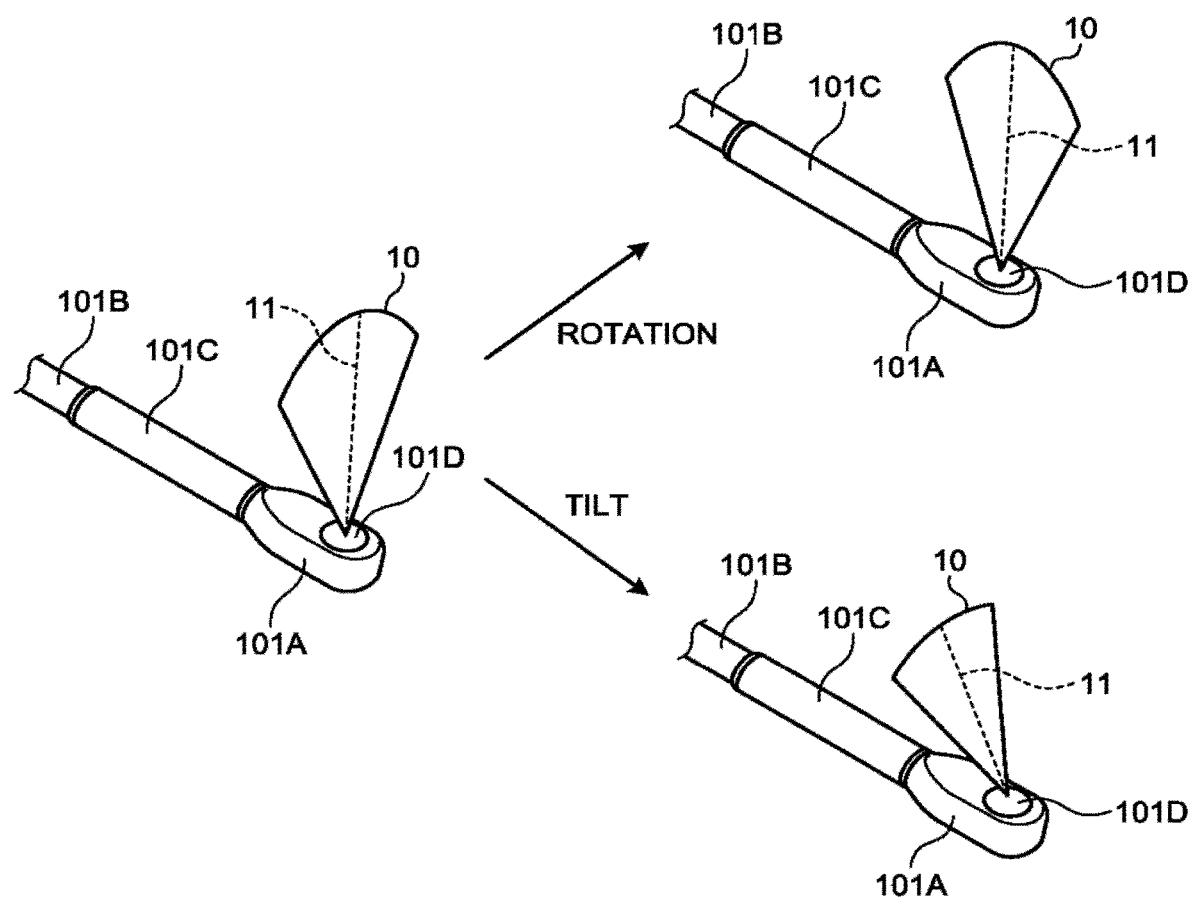
FIG. 2B is a diagram showing one example of the structure of the ultrasound probe according to the first embodiment.

A structure of the ultrasound probe 101 according to the first embodiment is explained, using FIG. 2A and FIG. 2B. FIG. 2A and FIG. 2B are diagrams showing one example of the structure of the ultrasound probe 101 according to the first embodiment. FIG. 2A shows an external view of the ultrasound probe 101 that is a TEE probe. FIG. 2B explains rotation and tilt of a scan region (scanning section) scanned by the ultrasound probe 101, which is a TEE probe.

As shown in FIG. 2A, the ultrasound probe 101 being a TEE probe includes a distal end portion 101A, a guide tube 101B, and a bending portion 101C. The distal end portion 101A is a portion that is brought into contact with an interior wall of the esophagus of the subject, and includes a transducer array 101D of a two-dimensional array. The guide tube 101B is a portion to insert the distal end portion 101A into an esophagus, and is constituted of a wiring and a tubular member that connect the distal end portion 101A and the apparatus main unit 100 (or a portion of the ultrasound probe 101 positioned outside a body). The bending portion 101C is a portion that connects the distal end portion 101A and the guide tube 101B, and has a mechanism of tilting the distal end portion 101A relative to the guide tube 101B. For example, the bending portion 101C tilts the distal end portion 101A in a front-and-back direction or in a left-and-right direction relative to the guide tube 101B. The front-and-back direction herein is a direction perpendicular to a surface of the transducer array 101D, and the left-and-right direction is a direction perpendicular to an axial direction of the guide tube 101B and to the front-and-back direction. A tilt angle of the distal end portion 101A (end portion angle) can be arbitrarily specified by an operator.

Furthermore, as shown in FIG. 2B, the ultrasound probe 101 being a TEE probe is structured to be able to rotate and tilt a scan region 10 in an arbitrary direction. For example, as shown in an illustration on the left in FIG. 2B, when the scan region 10 is set to an initial position, a center line 11 of the scan region 10 is perpendicular to the transducer array 101D, and an azimuth direction of the scan region 10 is perpendicular to the axial direction of the guide tube 101B. When the scan region 10 is rotated by 90°, for example, as shown in an illustration in the upper right in FIG. 2B, the azimuth direction of the scan region 10 becomes parallel to the axial direction of the guide tube 101B while the center line 11 staying perpendicular to the transducer array 101D. Moreover, when the scan region 10 is tilted, for example, as shown in an illustration in the lower right in FIG. 2B, the center line 11 is tilted while the azimuth direction of the scan region 10 staying perpendicular to the axial direction of the guide tube 101B. This rotation angle and the tilt angle can be arbitrarily specified by the operator.

Note that what has been explained with reference to FIG. 2A and FIG. 2B is only an example, and it is not limited to cases illustrated therein. For example, the ultrasound probe 101 can be a TEE probe that has a one-dimensional array in which multiple transducers are arranged in a single line. Furthermore, the ultrasound probe 101 can be a mechanical 4D (mecha4D probe) in which multiple piezoelectric transducers arranged in one line can be swung in a predetermined angle (swing angle).

The input device 102 includes a mouse, a keyboard, a button, a panel switch, a touch command screen, a foot switch, a trackball, a joystick, and the like, and accepts various kinds of setting requests from the operator of the ultrasonic diagnostic apparatus 1, and transfers the accepted various kinds of setting requests to the apparatus main unit 100.

The display 103 displays a graphical user interface (GUI) for the operator of the ultrasonic diagnostic apparatus 1 to input various kinds of setting requests by using the input device 102, or displays ultrasonic image data that is generated by the apparatus main unit 100, and the like. Furthermore, the display 103 displays various kinds of messages to notify the operator of processing states of the apparatus main unit 100. Moreover, the display 103 includes a speaker, and can output a sound also. For example, the speaker of the display 103 outputs predetermined sounds, such as a beep, to notify the operator of a processing state of the apparatus main unit 100.

The apparatus main unit 100 is an apparatus that generates ultrasonic image data based on a reflected-wave signal received by the ultrasound probe 101. The apparatus main unit 100 shown in FIG. 1 is an apparatus that can generate two-dimensional ultrasonic image data based on two-dimensional reflected-wave data received by the ultrasound probe 101.

The apparatus main unit 100 includes, as shown in FIG. 1, the transceiving circuitry 110, B-mode processing circuitry 120, doppler processing circuitry 130, image generating circuitry 140, storage circuitry 150, processing circuitry 160, and a communication interface 170. The transceiving circuitry 110, the B-mode processing circuitry 120, the doppler processing circuitry 130, the image generating circuitry 140, the storage circuitry 150, the processing circuitry 160, and the communication interface 170 are communicably connected to each other. Furthermore, the apparatus main unit 100 is connected to a network 5.

The transceiving circuitry 110 includes a pulse generator, a transmission delaying unit, a pulser, and the like, and provides a driving signal to the ultrasound probe 101. The pulse generator repeatedly generates rated pulses to generate transmission ultrasonic waves at a predetermined rate frequency. Moreover, the transmission delaying unit converges ultrasonic waves emitted from the ultrasound probe 101 into a beam, and gives delay time for each piezoelectric transducer necessary to determine a transmission directivity to each rated pulse generated by the pulse generator. Furthermore, the pulser applies a driving signal (driving pulse) to the ultrasound probe 101 in timing based on the rated pulse. That is, the transmission delaying unit arbitrarily adjusts a transmission direction of an ultrasonic wave transmitted from the surface of the piezoelectric transducer by varying the delay time to be given to each rated pulse.

The transceiving circuitry 110 has a function of instantaneously changing a transmission frequency, a transmission driving voltage, and the like to perform a predetermined scan sequence based on an instruction of the processing circuitry 160 described later. Particularly, the change of the transmission driving voltage is achieved by a linear amplifier transmission circuitry that can change the value instantaneously, or by a mechanism of electrically switching power source units.

Furthermore, the transceiving circuitry 110 includes a preamplifier, an analog/digital (A/D) converter, a reception delaying unit, an adder, and the like, and generates reflected-wave data by subjecting a reflected-wave signal received by the ultrasound probe 101 to various kinds of processing. The preamplifier amplifies the reflected-wave signal per channel. The A/D converter A/D converts the amplified reflected-wave signal. The reception delaying unit gives delay time necessary to determine a reception directivity. The adder generates reflected-wave data by performing addition processing of the reflected-wave signal processed by the reception delaying unit. By the addition processing of the adder, a reflection component from a direction according to the reception directivity of the reflected-wave signal is emphasized, a combined beam of transmission and reception of ultrasonic waves by the reception directivity and the transmission directivity.

The transceiving circuitry 110 causes the ultrasound probe 101 to transmit a two-dimensional ultrasonic beam when performing two-dimensional scanning of the subject P. The transceiving circuitry 110 then generates two-dimensional reflected-waved data from two-dimensional reflected-waved signal received by the ultrasound probe 101.

The form of an output signal from the transceiving circuitry 110 can take various forms, such as a signal including phase information called radio frequency (RF) signal, and an amplitude information subjected to envelope detection.

The B-mode processing circuitry 120 receives reflected-wave data from the transceiving circuitry 110, and performs logarithmic amplification, envelope detection processing, and the like to generate data (B-mode data) in which a signal intensity is expressed by a brightness level.

The doppler processing circuitry 130 performs frequency analysis on speed information in the reflected-wave data received from the transceiving circuitry 110, extracts, according to the Doppler effect, blood flow, tissue, and contrast agent echo components, and generates data (doppler data) obtained by extracting moving object information, such as speed, dispersion, and power at multiple points.

The B-mode processing circuitry 120 and the doppler processing circuitry 130 shown in FIG. 1 can process both two-dimensional reflected-waved data and three-dimensional reflected-wave data. That is, the B-mode processing circuitry 120 generates two-dimensional B-mode data from two-dimensional reflected-wave data, and generates three-dimensional B-mode data from three-dimensional reflected-wave data. Moreover, the doppler processing circuitry 130 generates two-dimensional doppler data from two-dimensional reflected-wave data, and generates three-dimensional doppler data from three-dimensional reflected-waved data.

The image generating circuitry 140 generates ultrasonic image data from data that is generated by the B-mode processing circuitry 120 and the doppler processing circuitry 130. That is, the image generating circuitry 140 generates two-dimensional B-mode image data in which an intensity of reflected wave is expressed by brightness from the two-dimensional B-mode data generated by the B-mode processing circuitry 120. Furthermore, the image generating circuitry 140 generates two-dimensional doppler image data expressing the moving object information from the two-dimensional doppler data generated by the doppler processing circuitry 130. The two-dimensional doppler image data is an image in which a speed image, a dispersion image, a power image, or an image of combination of these. The image generating circuitry 140 is also capable of generating M-mode image data from chronological data of B-mode data on one scanning line generated by the B-mode processing circuitry 120. Moreover, the image generating circuitry 140 can generate a doppler waveform in which speed information of blood flow and tissues are plotted chronologically based on the doppler data generated by the doppler processing circuitry 130.

Generally, the image generating circuitry 140 converts (scan converts) a scanning line signal string of ultrasound scanning into a scanning signal string of a video format typified by television and the like, and generates ultrasonic image data for display. Specifically, the image generating circuitry 140 performs coordinate conversion according to a scanning mode of ultrasonic waves by the ultrasound probe 101, and thereby generates ultrasonic image data for display. Moreover, as various types of image processing processes other than the scan convert process, the image generating circuitry 140 performs, for example, image processing (smoothing processing) to re-generate a brightness average-value image using multiple image frames subjected to the scan conversion, image processing (edge enhancement processing) by using a differential filter in an image, and the like. Furthermore, the image generating circuitry 140 adds character information of various parameters, a scale, a body mark, and the like to the ultrasonic image data.

That is, the B-mode data and the doppler data are ultrasonic image data before subjected to the scan conversion, and data that is generated by the image generating circuitry 140 is ultrasonic image data for display after subjected to the scan conversion. The B-mode data and the doppler data are also called raw data. The image generating circuitry 140 generates "two-dimensional B-mode image data and two-dimensional doppler image data" that are two-dimensional ultrasonic image data for display from "two-dimensional B-mode data and two-dimensional doppler data" that are two-dimensional ultrasonic image data before subjected to scan conversion.

Furthermore, the image generating circuitry 140 performs rendering processing on ultrasonic volume data to generate various kinds of two-dimensional image data to display the ultrasonic volume data on the display 103. The rendering processing performed by the image generating circuitry 140 includes processing of generating MPR image data from ultrasonic volume data by performing an MPR method. Moreover, the rendering processing performed by the image generating circuitry 140 includes processing of performing "curved MPR" on ultrasonic volume data, and processing of performing "maximum intensity projection" on ultrasonic volume data. Furthermore, the rendering processing performed by the image generating circuitry 140 includes volume rendering (VR) processing and surface rendering (SR) processing to generate two-dimensional image data in which three-dimensional information is reflected.

The storage circuitry 150 is a memory that stores image data for display that is generated by the image generating circuitry 140. Moreover, the storage circuitry 150 can store data that is generated by the B-mode processing circuitry 120 and the doppler processing circuitry 130 also. The B-mode data and the doppler data stored in the storage circuitry 150 are arranged to be retrievable by the operator after diagnosis, and are to be ultrasonic image data for display via the image generating circuitry 140.

Furthermore, the storage circuitry 150 stores various kinds of data, such as a control program to perform transmission and reception of ultrasonic waves, image processing and display processing, diagnosis information (for example, patient identification (ID), doctor's findings, and the like), diagnostic protocols, and various kinds of body marks. Moreover, data stored in the storage circuitry 150 can be transferred to an external device through an interface not shown. The external device is, for example, a personal computer (PC) that is used by a doctor performing diagnostic imaging, a storage medium such as a compact disk (CD) and a digital versatile disk (DVD), a printer, and the like.

The processing circuitry 160 controls overall processing of the ultrasonic diagnostic apparatus 1. Specifically, the processing circuitry 160 controls processing of the transceiving circuitry 110, the B-mode processing circuitry 120, the doppler processing circuitry 130, and the image generating circuitry 140 based on various kinds of setting requests input by the operator through the input device 102, and various kinds of control programs and various kinds of data read from the storage circuitry 150. Furthermore, the processing circuitry 160 controls to display the ultrasonic image data for display that is stored in the storage circuitry 150 on the display 103.

Moreover, the processing circuitry 160 performs an acquiring function 161, a setting function 162, a positioning function 163, and an output control function 164. The acquiring function 161 is one example of an acquiring unit. The setting function 162 is one example of a setting unit. Furthermore, the positioning function 163 is one example of a positioning unit. The output control function 164 is one example of an output control unit. Details of processing of the acquiring function 161, the setting function 162, the positioning function 163, and the output control function 164 performed by the processing circuitry 160 are described later.

Respective processing functions performed by the acquiring function 161, the setting function 162, the positioning function 163, and the output control function 164 that constitute the processing circuitry 160 shown in FIG. 1 are stored in the storage circuitry 150 in a form of computer-executable program. The processing circuitry 160 is a processor that implements functions corresponding to the respective programs by reading and executing the programs from the storage circuitry 150. In other words, the processing circuitry 160 that has read the respective programs is to have the respective functions shown in the processing circuitry 160 in FIG. 1.

The communication interface 170 is an interface to communicate with various kinds of devices in a hospital through the network 5. The processing circuitry 160 communicates with an external device by the communication interface 170. For example, the processing circuitry 160 receives medical image data (CT image data, magnetic resonance imaging (MRI) image data, and the like) that is acquired by the medical diagnostic imaging apparatus other than the ultrasonic diagnostic apparatus 1 through the network 5. The processing circuitry 160 then stores the received medical image data in the storage circuitry 150. Furthermore, the processing circuitry 160 displays the received medical image data on the display 103 together with ultrasonic image data that is acquired by itself. The medical image data to be displayed can be an image that is subjected to image processing (rendering processing) by the image generating circuitry 140. Furthermore, the medical image data to be displayed together with the ultrasonic image data can be acquired through a storage medium, such as a CD read-only memory (ROM), an MO, and a DVD.

In heart valve treatment, the ultrasonic diagnostic apparatus 1 and an X-ray CT apparatus are used in combination. For example, a doctor creates a treatment plan using CT image data (volume data) that is acquired by the X-ray CT apparatus before the operation, while referring to desired MPR images. During the operation, the doctor gives treatment, referring to the treatment plan created prior to the operation and real-time ultrasound images that are acquired by the ultrasonic diagnostic apparatus 1. It is preferable that the ultrasonic image to be displayed at this time be of the same cross section as that of the MPR images referred in the treatment planning.

However, it is difficult to acquire an ultrasonic image of the same cross section as that of the MPR images acquired before the operation. For example, because the TEE probe that is used in imaging a heart valve has limiting conditions in a part on which the probe can abut or in a movable range of the distal end portion 101A, it is difficult to image the same scan region (scanning section) as that MPR image generated arbitrarily from CT image data.

Therefore, the ultrasonic diagnostic apparatus 1 according to the first embodiment has the following processing functions to set a desired scan region easily. In the following, explanation is given with an imaging method using the ultrasound probe 101 of a TEE probe as an example, but embodiments are not limited thereto. For example, the following embodiment is widely applicable to imaging methods with limiting conditions, such as an imaging method using an enteral probe or a transvaginal probe, and an imaging method called apical approach in which imaging is performed between ribs.

Furthermore, in the following, setting processing of an objective scan region, and guiding processing to guide to an objective scan region are explained sequentially. The setting processing is processing to set an objective scan region to be a target of ultrasonic scanning on CT image data that is acquired prior to the operation. The guiding processing (navigation) is processing to bring a scan region that is actually scanned by the ultrasonic diagnostic apparatus 1 closer to the objective scan region set by the setting processing.

Setting Processing

First, the setting processing of an objective scan region is explained. The ultrasonic diagnostic apparatus 1 performs a following processing function as the setting processing. The acquiring function 161 acquires three-dimensional medical image data in which the subject P is imaged. Moreover, the setting function 162 sets an objective scan region to be a target of ultrasonic scanning in the three-dimensional medical image data based on limiting conditions relating to the ultrasonic scanning. Specifically, the setting function 162 extracts a three-dimensional area corresponding to a movable range from the three-dimensional medical image data based on the limiting conditions including a movable range of the ultrasound probe 101 with respect to the subject P, and sets an objective scan region according to the extracted three-dimensional region. In other words, the setting function 162 serving as the extracting unit extracts a movable range of the probe based on a structure of the subject shown in the three-dimensional medical image data. The setting function 162 serving as the setting unit sets a target scan region to be a target of scanning by the probe based on the extracted movable range. The objective scan region is also referred to as target scan region.

The limiting conditions include, for example, a "movable range" in a scan region with respect to a contact surface of the ultrasound probe 101, a "tiltable range of the ultrasound probe 101 with respect to the subject P, and a "scannable range" in a scan region. For example, in the imaging method using a TEE probe, the movable range is the interior wall of the esophagus. This interior wall of the esophagus differs per subject P (patient), and can be extracted from three-dimensional medical image data that is acquired in advance. Moreover, the tiltable range is determined by a limit value of a rotation angle and a limit value of a tilt range of a scan region with respect to an interior wall of an esophagus. The limit value of the rotation angle and the limit value of the tilt angle vary according to a type of the TEE probe, and can be acquired from product information of the TEE probe. Furthermore, the scannable range is determined by an azimuth direction and a length (distance) in a depth direction of a scan region, and can be acquired from product information of the TEE probe. There is a limiting condition that the shallowest part in the scannable range (hereinafter, described as "shallowest part") is a position in contact with a transducer and is included in the movable range. The limiting conditions are stored in advance in the storage circuitry 150 or a storage device that can be connected through the network 5. The stored limiting conditions can be arbitrarily changed as appropriate by the operator. Moreover, the movable range of the TEE probe is not limited to the interior wall of an esophagus. For example, a lumen of the esophagus can be extracted based on CT values. That is, the movable range of the TEE probe is only required to be a range including at least the lumen of the esophagus.

Note that the limiting conditions described above are one example in the case of using a TEE probe, and it is not limited thereto. For example, when an enteral probe or a transvaginal probe is used, the movable range is to be an interior wall of an intestine or a vagina. Moreover, in the case of the apical approach, the movable range is to be a portion between ribs. The tiltable range and the scannable range can be acquired from product information and the like, similarly to the case of a TEE probe.

Figure 4:
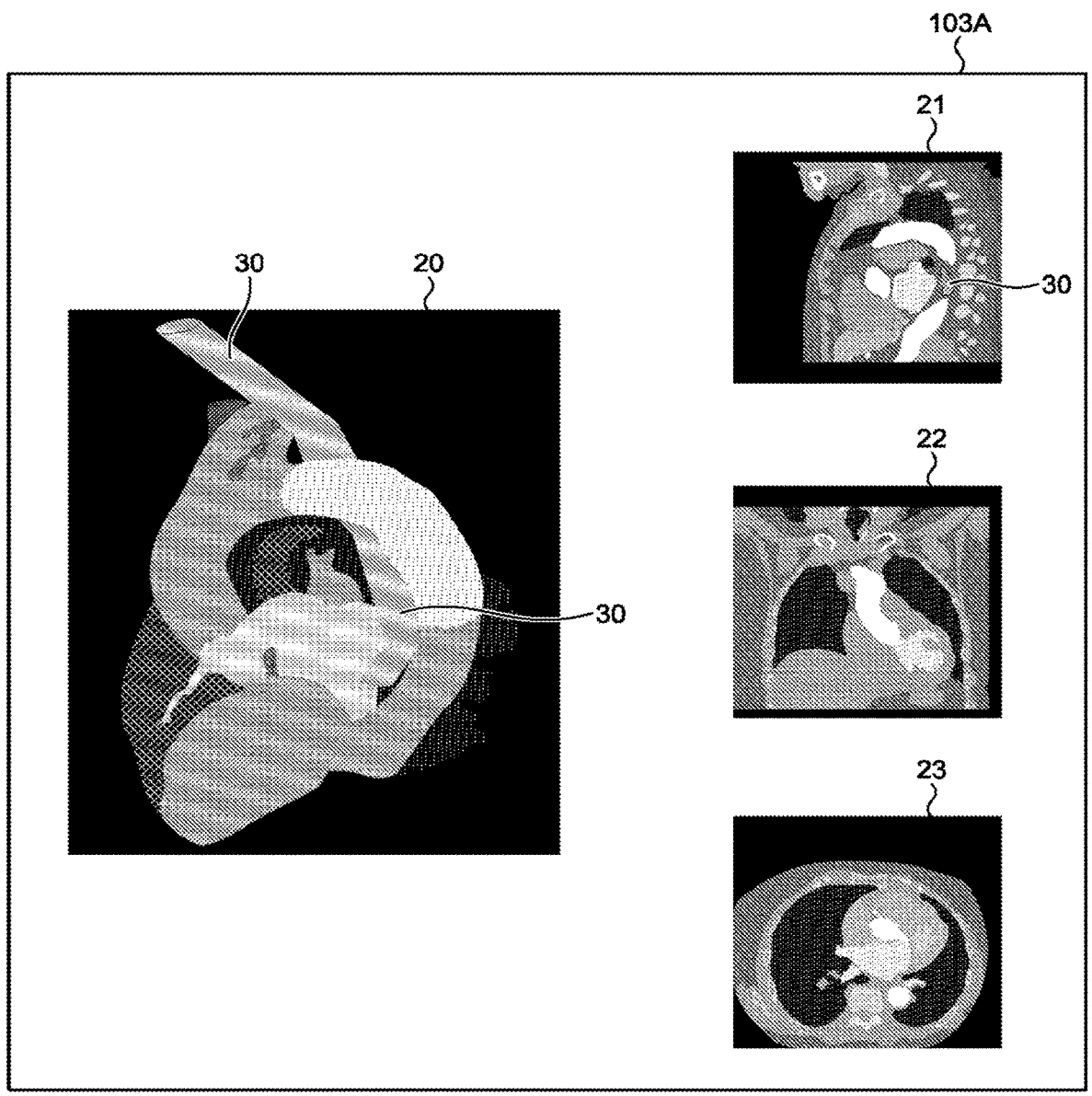
FIG. 4 is a diagram for explaining the setting processing in the ultrasonic diagnostic apparatus according to the first embodiment.
Figure 5:
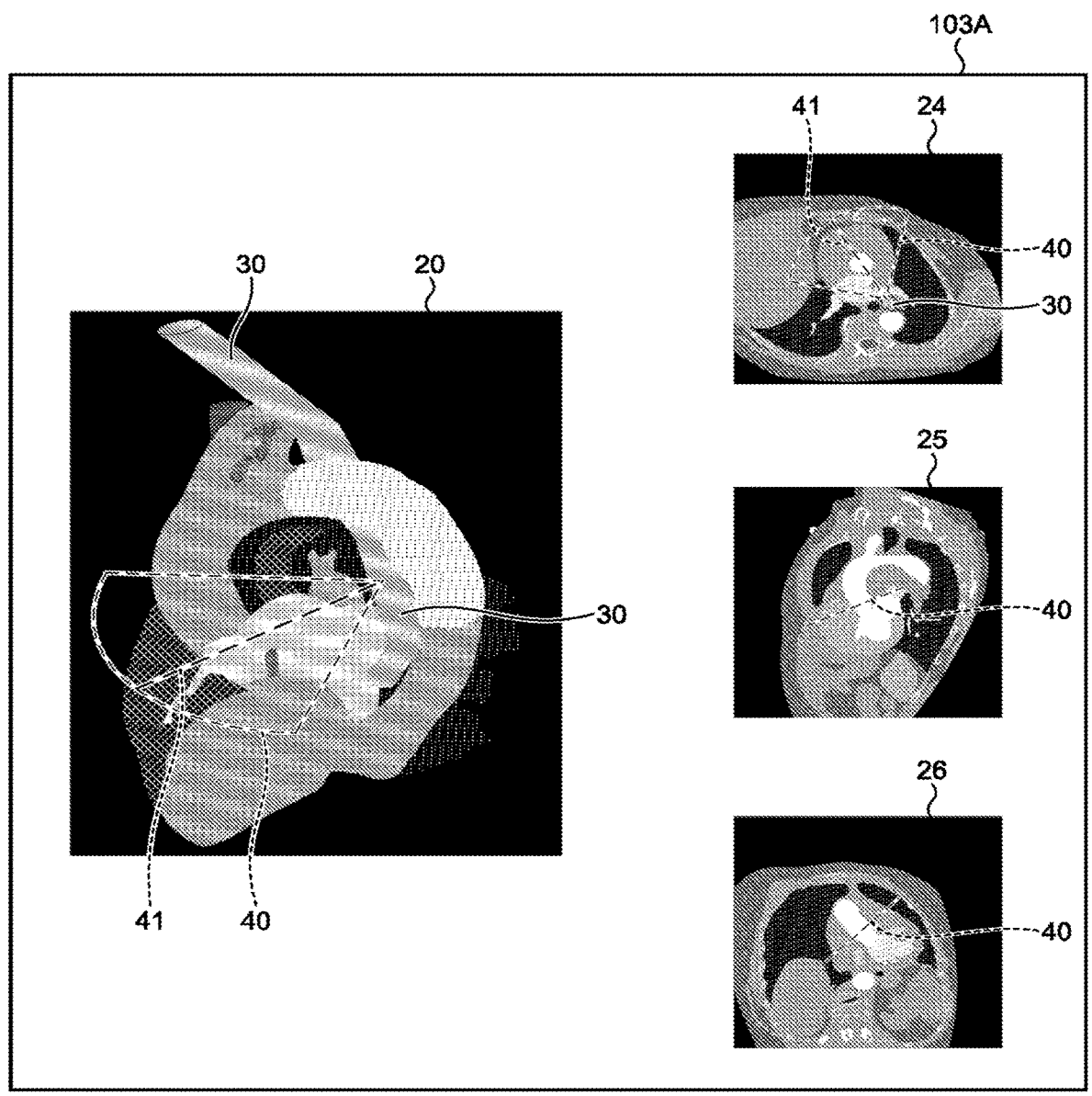
FIG. 5 is a diagram for explaining the setting processing in the ultrasonic diagnostic apparatus according to the first embodiment.

The setting processing in the ultrasonic diagnostic apparatus 1 according to the first embodiment is specifically explained, using FIG. 3. FIG. 3 is a flowchart showing a procedure of the setting processing in the ultrasonic diagnostic apparatus 1 according to the first embodiment. The procedure shown in FIG. 3 is started when an input instructing start of the setting processing is accepted from the operator. In FIG. 3, explanation is given, referring to FIG. 4 and FIG. 5. FIG. 4 and FIG. 5 are diagrams for explaining the setting processing in the ultrasonic diagnostic apparatus 1 according to the first embodiment.

In the following explanation of the setting processing, a case in which an objective scan region is set in CT image data is explained, but embodiments are not limited thereto. For example, the ultrasonic diagnostic apparatus 1 can set an objective scan region in three-dimensional medical image data in which the subject P is imaged by any medical diagnostic imaging apparatus, not limited to CT image data. For example, the ultrasonic diagnostic apparatus 1 can set an objective scan region in MR image data that is acquired by an MRI apparatus or three-dimensional image data that is acquired by the ultrasonic diagnostic apparatus 1.

At step S101, the processing circuitry 160 determines whether an input indicating start of the setting processing is accepted. For example, the operator inputs an instruction to start the setting processing by using the input device 102. The input device 102 outputs information indicating start of the setting processing input by the operator to the processing circuitry 160. The processing circuitry 160 determines that an input indicating start of the setting processing is received (step S101: YES) when information indicating start of the setting processing is accepted from the input device 102, and starts processing from step S102 and later. The processing circuitry 160 is in a standby state, suspending start of the processing at step S102 and later until an input indicating start of the setting processing is received (step S101: NO).

At step S102, the acquiring function 161 reads out CT image data. For example, the acquiring function 161 acquires the CT image data from the storage circuitry 150. The CT image data is, for example, image data in which a region (for example, chest) including the heart of the subject P is imaged by the X-ray CT apparatus. When CT image data is not stored in the storage circuitry 150, the acquiring function 161 can acquire it from an X-ray CT apparatus connected through the network 5, an external storage device for medical image data storage, or the like also.

At step S103, the setting function 162 extracts a region corresponding to the esophagus from the CT image data. For example, the setting function 162 performs segmentation processing on the CT image data acquired by the acquiring function 161, and thereby extracts a region corresponding to the esophagus of the subject P.

For example, as shown in FIG. 4, the setting function 162 displays VR image 20, MPR images 21, 22, 23 in a display region 103A of the display 103. The VR image 20 is a rendering image in which the heart and peripheral organs of the subject P are drawn. Moreover, the MPR images 21, 22, 23 are tomograms of a sagittal section, a coronal section, and an axial section of the chest of the subject P. The VR image 20 and the MPR images 21, 22, 23 are generated by various kinds of rendering processing on the CT image data acquired by the acquiring function 161.

For example, the operator specifies one point included in the region of the esophagus in the MPR images 21, 22, 23 in FIG. 4. In the example shown in FIG. 4, a part of the esophagus is drawn in the MPR image 21. Therefore, the operator brings a cursor to the region of the esophagus in the MPR image 21, and presses a button to specify one point. Thus, the setting function 162 recognizes that the point specified by the operator is a point included in the region of the esophagus. The setting function 162 then extracts an extraction region 30 corresponding to the esophagus from the CT image data by performing the segmentation processing to extract an image region having a CT value similar to that of the point specified by the operator. The setting function 162 displays (highlighting) the extraction region 30 on the VR image 20 and the MPR image 21.

As described, the setting function 162 extracts a three-dimensional region (the extraction region 30) corresponding to the movable range from three-dimensional medical image data. What is illustrated in FIG. 4 is only one example, and it is not limited to the illustration therein. For example, the case in which one point in the esophagus is specified in the MPR image 21 has been explained in FIG. 4. This is because the esophagus is drawn in the MPR image 21. Therefore, for example, when the esophagus is drawn in the MPR image 22 or the MPR image 23, the operator can specify one point in the esophagus in the MPR image 22 or the MPR image 23. Furthermore, when the esophagus is not drawn in any of the MPR images 21, 22, 23, the operator can search for a tomogram in which the esophagus is drawn by changing positions of respective tomograms to specify one point in the esophagus.

Moreover, the case in which the extraction region 30 is extracted manually has been explained in FIG. 4, but embodiments are not limited thereto, and the extraction region 30 can be extracted automatically. For example, the setting function 162 can extract the region of the esophagus automatically from three-dimensional medical image data based on the movable range, "the interior wall of the esophagus". In this case, the setting function 162 can extract the extraction region 30 automatically, by using CT values of the esophagus, physical characteristics, positional relationship with respect to other organs, such as the heart and the lung. Furthermore, the setting function 162 can prompt the operator to do the operation to specify one point in the esophagus by outputting a message of "please specify a region of esophagus" by an image or a voice.

At step S104, the setting function 162 accepts an input of a position of tomographic section. For example, the operator browses tomograms, to search for an appropriate tomogram to set an objective scan region. As a specific example, the operator inputs an instruction to tilt the MPR images 21, 22, 23 shown in FIG. 4.

At step S105, the setting function 162 changes the position of tomographic section of a display target within a range of the limiting conditions. For example, the setting function 162 changes the position of tomographic section to be displayed in the three-dimensional medical image data within a range satisfying the movable range and the tiltable range.

For example, the setting function 162 determines whether the position of tomographic section input at step S104 satisfies the limiting conditions. Specifically, the setting function 162 determines whether the tomogram at the input position of tomographic section includes the extraction region 30, and whether the angle of the position of tomographic section relative to the interior wall of the esophagus is included in the tiltable range. When the both conditions are satisfied, that is, when the tomogram includes the extraction region 30 and the angle of the position of tomographic section is included in the tiltable range, the setting function 162 determines that the limiting conditions are satisfied. When the limiting conditions are satisfied, the setting function 162 changes the position of tomographic section to be displayed. When the limiting conditions are not satisfied, the setting function 162 does not change the input position of tomographic section.

As described, the setting function 162 changes the position of tomographic section in which the objective scan region is set in the three-dimensional medical image data within the range satisfying the limiting conditions.

At step S106, the setting function 162 displays the tomogram corresponding to the position of tomographic section. For example, the setting function 162 displays a tomogram corresponding to the position of tomographic section changed at step S105 in the display region 103A.

For example, as shown in FIG. 5, the setting function 162 displays an MPR image 24 instead of the MPR images 21, 22, 23 shown in FIG. 4. The MPR image 24 is a tomogram corresponding to the position of tomographic section that is specified by the operator to set an objective scan region 40. In the MPR image 24, the extraction region 30 is drawn. In this case, the objective scan region 40 and a center line 41 are not drawn in the MPR image 24 yet.

At step S107, the setting function 162 determines whether a position of tomographic section is decided. For example, when the operator views the MPR image 24 and determines to be appropriate as a cross section in which the objective scan region 40 is set, the operator presses a confirmation button. Thus, the setting function 162 determines that the position of tomographic section is decided (step S107: YES), and shifts to processing at step S108. When the position of tomographic section is not decided (step S107: NO), the setting function 162 repeats the processing at step S104 to step S106 until the position of tomographic section is decided. That is, the operator can change the position of tomographic section to an arbitrary position within the range of the limiting conditions until the position of tomographic section is decided.

At step S108, the setting function 162 displays the preset objective scan region 40 on the tomogram. For example, when the position of tomographic section is decided by the operator, the setting function 162 displays the objective scan region 40 on the MPR image 24 and the VR image 20 as shown in FIG. 5. For the preset objective scan region 40, for example, the direction of the center line 41, the length (width) of in the azimuth direction, and the length in the depth direction are defined, and the shallowest part is positioned to be included in the extraction region 30. The setting function 162 displays MPR images 25, 26. The MPR image 25 is a perpendicular cross section that is perpendicular to the MPR image 24 passing through the center line 41. Moreover, the MPR image 26 is a perpendicular cross section that is perpendicular to the center line 41 and the MPR image 24. The setting function 162 displays a broken line indicating the position of the objective scan region 40 on the MPR images 25, 26 also.

At step S109, the setting function 162 accepts an input of a position, a direction, or a size of the objective scan region 40. For example, the operator translates the objective scan region 40 on the MPR image 24. Furthermore, the operator rotates the center line 41 about the shallowest part. Moreover, the operator changes the width in the azimuth direction and the length in the depth direction. Thus, the setting function 162 accepts an input of a position change, rotation, a change in the size of the objective scan region 40.

At step S110, the setting function 162 changes the position, direction, or size of the objective scan region 40 within the range of the limiting conditions. For example, the setting function 162 sets the objective scan region 40 such that the shallowest part of the objective scan region 40 is included in a three-dimensional region (the extraction region 30). Furthermore, for example, the setting function 162 sets the shallowest part, the scanning direction, the width in the azimuth direction, and the length in the depth direction of the objective scan region 40 within the range satisfying the scannable range.

For example, the setting function 162 determines whether the position, the direction, or the size of the objective scan region 40 input at step S109 satisfies the limiting condition. Specifically, the setting function 162 determines whether the input shallowest part of the objective scan region 40 is included in the extraction region 30. When the shallowest part is included in the extraction region 30, the setting function 162 determines that the position of the objective scan region 40 satisfies the limiting conditions, and changes it to the input position of the objective scan region 40. Moreover, the setting function 162 determines whether the input azimuth direction and size (length) in the depth direction of the objective scan region 40 satisfy the scannable range. When the azimuth direction and the length in the depth direction satisfy the scannable range, the setting function 162 changes them to the input azimuth direction and size in the depth direction of the objective scan region 40.

As described, the setting function 162 sets the objective scan region 40 on a position of tomographic section within a range satisfying the limiting conditions. That is, the setting function 162 extracts at least a lumen of the esophagus of the subject P as a three-dimensional region, and sets a region in which a transesophageal probe positioned in the lumen can perform ultrasonic scanning based on the extracted lumen, the tiltable range, and the scannable range. In this case, the region in which the ultrasonic scanning can be performed is a scannable region by a TEE probe that is inserted to the lumen of the esophagus, and is a region in a substantially cylindrical shape (a cylindrical shape warped along the esophagus) wider than the lumen of the esophagus. Furthermore, the setting function 162 can display the region in which ultrasonic scanning can be performed on the display 103. For example, the setting function 162 can display the region in which ultrasonic scanning can be performed on the VR image 20, or can display a tomographic section of the region in which ultrasonic scanning can be performed on the MPR images 21, 22, 23.

What is illustrated in FIG. 5 is only an example, and it is not limited the illustration. For example, the case in which the MPR images 21, 22, 23 are not displayed has been explained in FIG. 5, but it is not limited thereto. For example, the setting function 162 can display, when setting the objective scan region 40, the VR image 20 and the MPR images 21, 22, 23, 24, 25, 26 at the same time in the display region 103A. Furthermore, the operator can arbitrarily set which image to display each time.

At step S111, the setting function 162 determines whether to readjust the position of tomographic section. For example, when the operator views the objective scan region 40 and determines that the position of tomographic section of the objective scan region 40 is inappropriate, the operator inputs an instruction to readjust the position of tomographic section. Thus, the setting function 162 determines to readjust the position of tomographic section (step S111: YES), and shifts to processing at step S104. When the position of tomographic section is not readjusted (step S111: NO), the setting function 162 shifts to processing at step S112.

At step S112, the setting function 162 determines whether the objective scan region 40 is decided. For example, when the operator views and determines that the objective scan region 40 is appropriate, the operator presses the confirmation button. Thus, the setting function 162 determines that the objective scan region 40 is decided (step S112: YES), and ends the setting processing of the objective scan region 40. When the position of tomographic section is not decided (step S112: NO), the setting function 162 repeats the processing at step S109 to S11 until the objective scan region 40 is decided. That is, the operator can change the position of tomographic section and the objective scan region 40 within the range of the limiting conditions until the objective scan region 40 is decided.

The procedure shown in FIG. 3 is only an example, and embodiments are not limited thereto. For example, the procedure described above can be changed appropriately within a range not causing contradictions in the processing.

Moreover, the case in which the setting processing is performed in the ultrasonic diagnostic apparatus 1 has been explained in FIG. 3, but embodiments are not limited thereto. For example, the setting processing shown in FIG. 3 can be performed in other medical-image processing apparatuses, such as a work station and a console device of an X-ray CT apparatus. In this case, information indicating the position of the objective scan region 40 set on CT image data is output to the ultrasonic diagnostic apparatus 1 together with the CT image data, and is used in the guiding processing explained later.

Furthermore, the case in which the position of tomographic section and the objective scan region 40 are set within the range satisfying the limiting conditions by excluding a position of tomographic section and the objective scan region 40 out of the range of the limiting conditions from the display has been explained in FIG. 3, but embodiments are not limited thereto. For example, the setting function 162 can display a position of tomographic section and the objective scan region 40 desired by the operator regardless of the limiting conditions, and can determine whether the limiting conditions are satisfied at the point of time when the position of tomographic section and the objective scan region 40 are confirmed to be decided. That is, when the position of tomographic section and the objective scan region 40 set by the operator do not satisfy the limiting conditions, the fact is informed, and the operator repeats re-setting a position of tomographic section and the objective scan region 40 until the limiting conditions are satisfied.

Guiding Processing

Next, the guiding processing to the objective scan region 40 is explained. The ultrasonic diagnostic apparatus 1 performs a following processing function as the guiding processing. That is, the positioning function 163 performs positioning of ultrasonic image data that is collected by ultrasonic scanning and three-dimensional medical image data. Furthermore, the output control function 164 outputs guiding information to bring a scan region corresponding to the ultrasonic image data closer to the objective scan region 40 based on a difference between a scan region corresponding to the ultrasonic image data subjected to the positioning and the objective scan region 40 set in the three-dimensional medical image data subjected to positioning.

Figure 6:
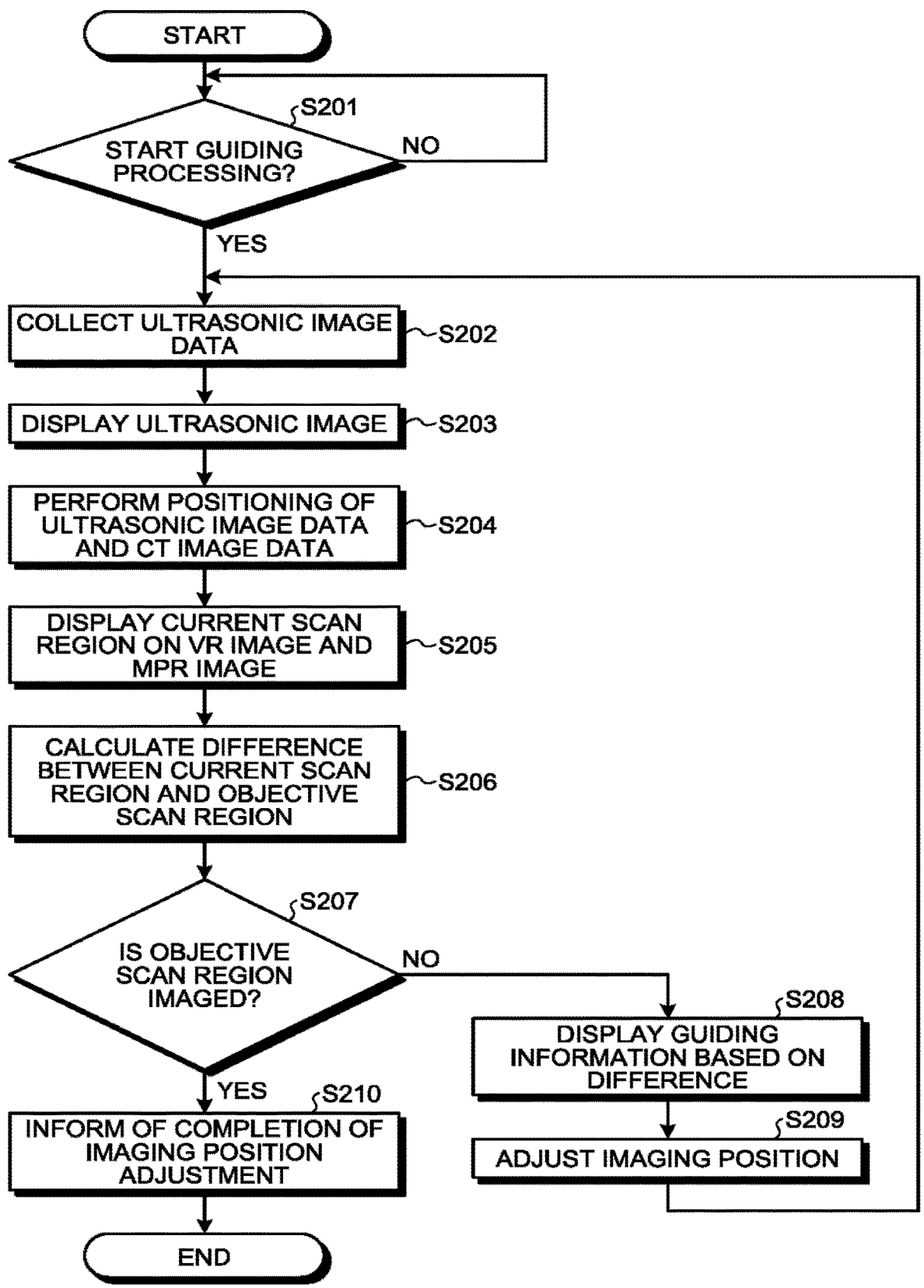
FIG. 6 is a flowchart of a procedure of guiding processing in the ultrasonic diagnostic apparatus according to the first embodiment.
Figure 7:
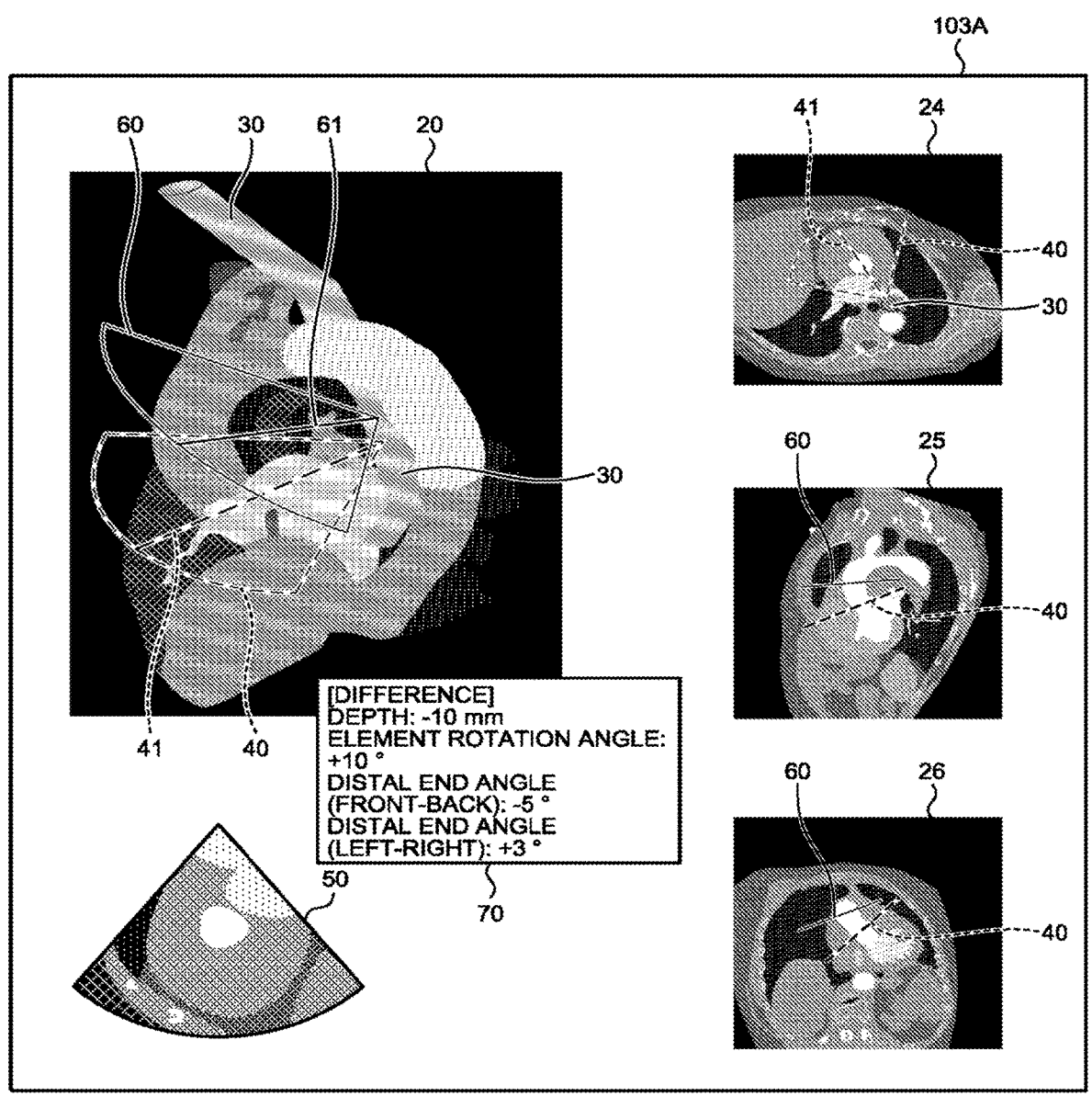
FIG. 7 is a diagram for explaining the guiding processing in the ultrasonic diagnostic apparatus according to the first embodiment.

The guiding processing in the ultrasonic diagnostic apparatus 1 according to the first embodiment is specifically explained, using FIG. 6. FIG. 6 is a flowchart of a procedure of the guiding processing in the ultrasonic diagnostic apparatus 1 according to the first embodiment. The procedure shown in FIG. 6 is started when an input indicating start of the guiding processing is accepted. Explanation is given in FIG. 6, referring to FIG. 7. FIG. 7 is a diagram for explaining the guiding processing in the ultrasonic diagnostic apparatus 1 according to the first embodiment. Note that when the guiding processing is performed, the information set in the setting processing is displayed in advance in the display region 103A of the display 103. For example, in FIG. 7, the VR image 20, the MPR images 24, 25, 26 are displayed, and the extraction region 30, the objective scan region 40, and the center line 41 are displayed on these images.

At step S201, the processing circuitry 160 determines whether an input indicating start of the guiding processing is accepted from the operator. For example, the operator inputs an instruction for start of the guiding processing by using the input device 102. The input device 102 outputs information indicating start of the guiding processing input by the operator to the processing circuitry 160. The processing circuitry 160 determines that an input indicating start of the guiding processing is accepted when the information indicating start of the guiding processing is accepted from the input device 102, and starts processing at step S202 and later. The processing circuitry 160 is in a standby state without starting the processing at step S202 and later until an input indicating start of the guiding processing is accepted.

At step S202, the processing circuitry 160 collects ultrasonic image data. For example, the processing circuitry 160 controls the transceiving circuitry 110 to cause the ultrasound probe 101 to perform ultrasonic scanning, and collects B-mode image data of a current frame.

At step S203, the processing circuitry 160 displays an ultrasonic image. For example, the processing circuitry 160 displays an ultrasonic image 50 in the display region 103A of the display 103 as shown in FIG. 7.

At step S204, the positioning function 163 performs positioning of the ultrasonic image data and the CT image data. For example, the positioning function 163 performs the positioning by pattern matching between the ultrasonic image data and the CT image data. Specifically, the positioning function 163 extracts characteristic regions from each of the ultrasonic image data and the CT image data, and searches for similar regions among the extracted regions, thereby performing the positioning of the ultrasonic image data and the CT image data. The positioning function 163 can perform the positioning using any conventional technique, not limited to pattern matching. For example, when a position sensor (magnetic sensor, or the like) is mounted on the ultrasound probe 101, the positioning can be performed by using position information.

At step S205, the output control function 164 displays a current scan region 60 on the VR image 20 and the MPR images 24, 25, 26. For example, as shown in FIG. 7, the output control function 164 displays the scan region 60 corresponding to current B-mode image data, and a center line 61 thereof on the VR image 20 and the MPR images 24, 25, 26 as shown in FIG. 7. That is, the output control function 164 serving as the display control unit displays a target scan region in three-dimensional medical image data.

At step S206, the output control function 164 calculates a difference between the current scan region 60 and the objective scan region 40. For example, the output control function 164 calculates a difference in the depth direction as "−10 mm", a difference in an element rotation angle expressing the rotation angle of the scan region 60 as "+10°", a difference in a distal end angle (front-back) being an angle in the front-and-back direction of the distal end portion 101A as "5°", and a difference in a distal end angle (left-right) being an angle in the left-and-right direction of the distal end portion 101A as "+3°".

At step S207, the output control function 164 determines whether the objective scan region 40 is imaged. For example, the output control function 164 determines whether positions, directions, and sizes of the current scan region 60 and the objective scan region 40 are matching with each other. When not matching (step S207: NO), the output control function 164 shifts to processing at step S208. On the other hand, when matching (step S207: YES), the output control function 164 shifts to processing at step S210. "Matching" herein is not limited to complete matching without the least difference, but can include an allowable level of errors.

At step S208, the output control function 164 displays guiding information based on the differences. For example, as shown in FIG. 7, the output control function 164 displays guiding information 70 in the display region 103A. In the guiding information 70, difference information calculated at step S"06 is given. The guiding information 70 is not limited to the illustrated example. For example, items given in the guiding information 70 can be changed arbitrarily. Moreover, the guiding information 70 is not necessarily required to be output as numeric value information, and can be output, for example, as an image of arrows according to a difference, or can be output as a voice reading the difference.

At step S209, the operator adjusts an imaging position. For example, the operator operates the ultrasound probe 101 of a TEE probe such that the difference described in the guiding information 70 decreases. Thus, the operator brings the current scan region 60 closer to the objective scan region 40. The processing circuitry 160 then shifts to the processing at step S202, and repeats the processing at step S202 to S209 until the current scan region 60 and the objective scan region 40 match with each other (step S207: YES).

At step S210, the output control function 164 informs of completion of adjustment of the imaging position. For example, the output control function 164 informs, when the current scan region 60 and the objective scan region 40 become matching with each other, the completion of adjustment of the imaging position by highlighting the current scan region 60. The processing circuitry 160 then ends the guiding processing. After the guiding processing is ended, the ultrasonic diagnostic apparatus 1 performs collection of ultrasonic image data for diagnosis (or operation) of the subject P as appropriate.

The procedure shown in FIG. 6 is only an example, and embodiments are not limited thereto. For example, the procedure described above can be changed appropriately within a range not causing contradictions in the processing.

For example, the case in which the operator manually adjusts an imaging position has been explained at step S209 in FIG. 6, but embodiments are not limited thereto. For example, when it is electronically adjustable, the output control function 164 can adjust an imaging position automatically. For example, when ultrasonic scanning is performed by a two-dimensional array probe or a mecha4D probe, the output control function 164 can bring the scan region 60 closer to the objective scan region 40 by controlling an electronic scanning of the two-dimensional array probe, or a swinging direction of the mecha4D probe.

As described above, in the ultrasonic diagnostic apparatus 1 according to the first embodiment, the acquiring function 161 acquires three-dimensional medical image data in which the subject P is imaged. Moreover, the setting function 162 sets the objective scan region 40 to be a subject of ultrasonic scanning in the three-dimensional medical image data based on limiting conditions relating to the ultrasonic scanning. According to this arrangement, the ultrasonic diagnostic apparatus 1 according to the first embodiment can set a desired scan region easily. For example, because the objective scan region 40 is set, even when there are limiting conditions in an imaging method as in the case of a TEE probe, within a range of the limiting conditions in an abuttable portion or in a movable range of the distal end portion 101A, the ultrasonic diagnostic apparatus 1 can image a scan region same as that of an MPR image that is arbitrarily generated from CT image data easily.

Moreover, in the ultrasonic diagnostic apparatus 1 according to the first embodiment, the positioning function 163 performs positioning of ultrasonic image data collected by ultrasonic scanning and three-dimensional medical image data. Furthermore, the output control function 164 outputs the guiding information to bring a scan region corresponding to the ultrasonic image data closer to the objective scan region 40 based on a difference between the scan region corresponding to the ultrasonic image data subjected to the positioning and the objective scan region 40 set in the three-dimensional medical image data subjected to the positioning. According to this arrangement, even when there are limiting conditions in an imaging method as in the case of a TEE probe, the ultrasonic diagnostic apparatus 1 according to the first embodiment can acquire a scan region same as that of an MPR image that is arbitrarily generated from CT image data easily.

Second Embodiment

The case in which the single objective scan region 40 is set has been explained in the first embodiment, but embodiments are not limited thereto. For example, the ultrasonic diagnostic apparatus 1 is applicable also to a case in which more than one objective scan region 40 is set.

The ultrasonic diagnostic apparatus 1 according to a second embodiment has a structure similar to that of the ultrasonic diagnostic apparatus 1 shown in FIG. 1, but a part of the processing of the setting function 162 and the output control function 164 is different therefrom. Therefore, points that differ from the first embodiment are mainly explained in the second embodiment, and explanation about points having functions similar to those in the structure explained in the first embodiment is omitted.

The setting function 162 according to the second embodiment sets the multiple objective scan regions 40. For example, the operator sets the objective scan region 40 for the middle of operation and the objective scan region 40 for post-operation individually. The objective scan region 40 for the middle of operation corresponds to, for example a scan region to observe a heart valve. Moreover, the objective scan region 40 for post-operation corresponds to, for example, a scan region to observe blood flow conditions (whether regurgitation is observed). As the setting function 162 basically performs the same processing as the processing explained in the first embodiment except a point that more than one objective scan region 40 is set, detailed explanation is omitted.

When the multiple objective scan regions 40 are set, the output control function 164 according to the second embodiment sequentially outputs respective guiding information for the respective objective scan regions 40. For example, the operator selects the objective scan region 40 for the middle of operation as a subject of guiding during an operation. The output control function 164 calculates a difference between the selected objective scan region 40 for the middle of operation and the scan region 60 corresponding to the current ultrasonic image data. The output control function 164 then outputs the guiding information based on the calculated difference. Thus, the operator performs an operation after moving the current scan region 60 to the position of the objective scan region 40 for the middle of operation.

Furthermore, when the operation is finished, the operator selects the objective scan region 40 for post-operation as a subject of guiding. The output control function 164 calculates a difference between the selected objective scan region 40 for post-operation and the scan region corresponding to the current ultrasonic image data. The output control function 164 then outputs the guiding information based on the calculated difference. Thus, the operator observes post-operation blood flow after moving the current scan region 60 to the position of the objective scan region 40 for post-operation.

As described, the ultrasonic diagnostic apparatus 1 according to the second embodiment sets the multiple objective scan regions 40, and outputs the guiding information based on a difference between a subject scan region selected from among the objective scan regions 40 and a scan region corresponding to ultrasonic image data. Thus, for example, the operator can perform imaging easily even when the multiple objective scan regions 40 are present.

The above explanation is only an example, and it is not limited to what is explained above. For example, the case in which the two objective scan regions 40 are set for the middle of operation and for post-operation has been explained in the example described above, embodiments are not limited thereto. For example, not limited to uses (timing) such as the middle of operation and post-operation, the objective scan region 40 can be set in the arbitrary number.

Moreover, the case in which the guiding processing is performed sequentially one by one for the multiple objective scan regions 40 has been explained in the example described above, but embodiments are not limited thereto. For example, the guiding processing for the multiple objective scan regions 40 can be parallelly performed at the same time. That is, the output control function 164 can output multiple pieces of the guiding information to bring a scan region of an ultrasound probe closer to the respective objective scan regions based on differences between the respective objective scan regions and the scan region corresponding to the ultrasonic image data. IN this case, for example, the same number of pieces of the guiding information 70 as the number of the objective scan regions 40 are displayed in the display region 103A.

Third Embodiment

Moreover, the case in which a single piece of three-dimensional image data is used has been explained in the embodiments described above, but embodiments are not limited thereto. For example, the ultrasonic diagnostic apparatus 1 can use more than one piece of three-dimensional image data.

For example, in an operation of a heart valve, a technique called rapid pacing in which blood flow is temporarily suppressed by stimulating a heart with high frequency can be used. In this case, different from normal beats, the heart is convulsed. Accordingly, it is impossible to estimate what type of heart makes what type of convulsion in the rapid pacing and, therefore, it is difficult to determine a cardiac phase of three-dimensional medical image data acquired in advance to one time phase.

Therefore, in the third embodiment, three-dimensional medical image data of multiple cardiac phases are acquired in advance, and the objective scan region 40 for reference is set to each piece of the three-dimensional medical image data. In an operation, data of a cardiac phase similar to the state of the heart during the rapid pacing is selected from among the three-dimensional medical image data of multiple cardiac phases to use as a reference.

That is, the acquiring function 161 according to the third embodiment acquires multiple pieces of three-dimensional medical image data in which a region including the heart of the subject P is imaged at multiple cardiac phases different from each other. The operator sets the objective scan region 40 in each of the acquired multiple pieces of the three-dimensional medical image data.

The setting function 162 uses, when a cardiac phase for which the objective scan region 40 has already been set is present among the multiple cardiac phases, the objective scan region 40 already set as an initial position to set the objective scan region 40 for other cardiac phases. That is, when the multiple pieces of the three-dimensional medical image data include three-dimensional medical image data in which an objective scan region has been set and three-dimensional medical image data in which an objective scan region has not been set, the setting function 162 uses information about the objective scan region already been set as the initial position to set an objective scan region in three-dimensional medical image data in which an objective scan region has not been set yet.

For example, there is a case in which four pieces of CT image data of a first to a fourth cardiac phases are acquired as three-dimensional medical image data of multiple cardiac phases. In this case, the setting function 162 sets the objective scan region 40 for the CT image data of the first cardiac phase similarly to the setting processing explained in the first embodiment. The setting function 162 then uses information about the objective scan region 40 set for the first cardiac phase as an initial position to set the objective scan region 40 for the CT image data of the second to the fourth cardiac phases.

Specifically, the objective scan region 40 already been set includes information, such as a position of tomographic section, a direction of the center line 41 relative to the esophagus (the extraction region 30), and a size of the objective scan region 40. Therefore, the setting function 162 sets an initial position of the objective scan region 40 by applying the information such as the position of tomographic section, the direction of the center line 41 relative to the esophagus (the extraction region 30), and the size of the objective scan region 40 to the CT image data of the second to the fourth cardiac phases. Thus, the operator can set the objective scan region 40 easily.

The positioning function 163 performs positioning of three-dimensional medical image data selected from among data of the multiple cardiac phases and ultrasonic image data. For example, when the first cardiac phase is selected by the operator from among the first to the fourth cardiac phases, the positioning function 163 performs positioning of the CT image data of the first cardiac phase and current B-mode image data.

Sequentially, the output control function 164 outputs the guiding information 70 based on a difference between the objective scan region 40 of a cardiac phase selected from among the multiple cardiac phases and a scan region corresponding to ultrasonic image data. For example, when the first cardiac phase is selected by the operator from among the first to the fourth cardiac phases, the output control function 164 outputs the guiding information 70 based on a difference between the objective scan region 40 of the first cardiac phase and the current scan region 60. Thus, the operator can select a cardiac phase similar to a state of a heart during the rapid pacing appropriately to user as a reference.

Other Embodiments

In addition to the embodiments described above, it can be implemented by various different embodiments.

Application to Medical Image-Processing Apparatus

Among the processing explained in the embodiments described above, the setting processing can be implemented similarly in a medical image-processing apparatus also.

Figure 8:
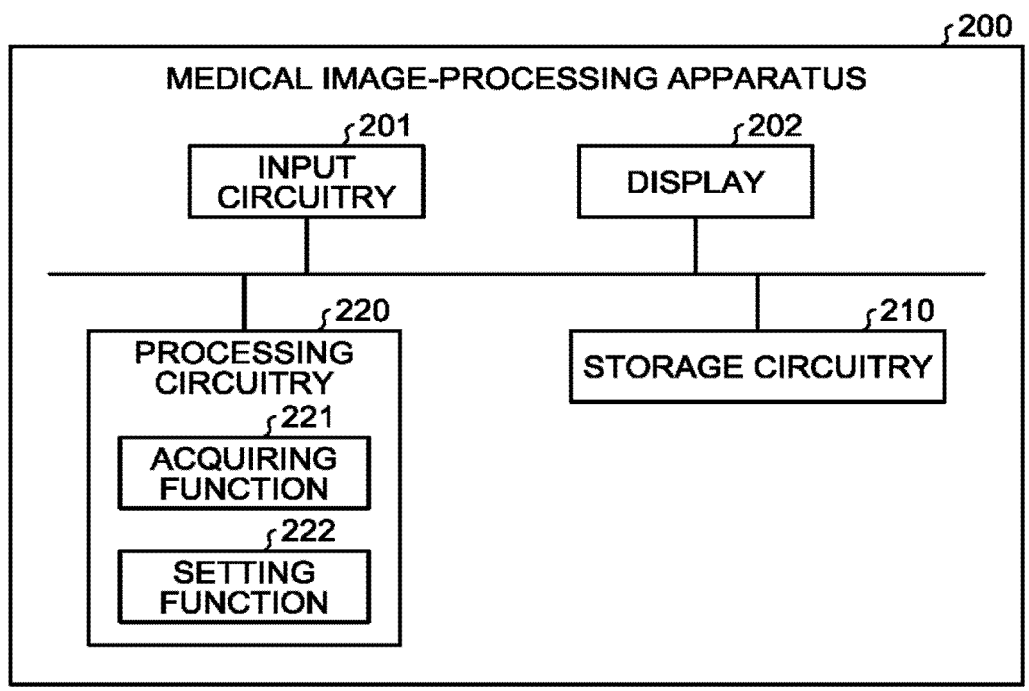
FIG. 8 is a block diagram showing a configuration example of a medical image-processing apparatus according to another embodiment.

FIG. 8 is a block diagram showing a configuration example of a medical image-processing apparatus 200 according to another embodiment. The medical image-processing apparatus 200 corresponds to, for example, an information processing apparatus, such as a personal computer and a workstation, or a control device of a medical diagnostic imaging apparatus, such as a console device included in an X-ray CT apparatus.

As shown in FIG. 8, the medical image-processing apparatus 200 includes input circuitry 201, a display 202, storage circuitry 210, and processing circuitry 220. The input circuitry 201, the display 202, the storage circuitry 210, and the processing circuitry 220 are communicably connected to each other.

The input circuitry 201 is an input device, such as a mouse, a keyboard, and a touch panel, to accept various kinds of instructions and setting requests from the operator. The display 202 is a display device that displays medical images, and that displays a GUI for the operator to input various kinds of setting requests by using the input circuitry 201.

The storage circuitry 210 is, for example, a NAND (Not And) flash memory or a hard disk drive (HDD), and stores various kinds of programs to display medical image data and a GUI, and information used by the programs.

The processing circuitry 220 is an electronic device (processor) to control the overall processing in the medical image-processing apparatus 200. The processing circuitry 220 performs an acquiring function 221 and a setting function 222. The respective processing functions performed by the processing circuitry 220 are stored in the storage circuitry 210 in a form of computer-executable program. The processing circuitry 220 implements functions corresponding to the respective programs by reading and executing the programs.

For example, the acquiring function 221 can perform basically the same processing as the acquiring function 161 shown in FIG. 1. That is, the acquiring function 221 acquires three-dimensional medical image data in which a subject is imaged. Moreover, the setting function 222 can perform basically the same processing as the setting function 162 shown in FIG. 1. That is, the setting function 222 sets an objective scan region to be a subject of ultrasonic scanning in three-dimensional medical image data. According to this arrangement, the medical image-processing apparatus 200 can set a desired scan region easily.

Although it is explained that the respective processing functions explained below are implemented by a single unit of the processing circuitry 160 in the present embodiment, the processing circuitry can be configured by combining multiple independent processors to implement the functions by the respective processors executing the programs.

Application to Other Medical Diagnostic-Imaging Apparatuses

In the above embodiments, the case in which the functions according to the embodiments are applied to the ultrasonic diagnostic apparatus 1 has been explained, but it is not limited thereto. For example, the functions according to the embodiments are also applicable to other medical diagnostic-imaging apparatuses. For example, the other medical diagnostic-imaging apparatuses include an intravascular ultrasoundscan (IVUS), an optical coherence tomography (OCT), an endoscope, and the like.

IVUS is a technique in which a micro-ultrasonic transducer is guided into a blood vessel lumen, ultrasonic waves are transmitted and received in a 360 degree direction from the transducer, to acquire a tomogram in a disk shape corresponding to a minor axis direction of the blood vessel. In IVUS, a probe to be guided into a blood vessel lumen is used, and the blood vessel of a subject corresponds to a movable range. Moreover, a target scan region in IVUS is defined based on a position on a core line of the blood vessel, a distance from the position (corresponding to a radius of the disk shape).

OCT is a technique of acquiring a precise tomogram of a tissue under noninvasive condition based on the principle of interferometer using reflected light of near infrared ray that passes well through a tissue of a living body. IN OCT, a probe that performs scanning by near infrared rays is used, when the probe of OCT is inserted into a body of a subject to perform imaging, a lumen, such as an esophagus and an intestine, corresponds to a movable range. Furthermore, a target scan region in OCT is defined based on a position on a core line of a lumen region, an irradiation direction of near infrared rays from the position, an irradiation range, and the like.

The endoscope is an optical device to observe the inside of a subject body, such as a lumen region of an esophagus and an intestine and an incised portion on a body surface. The endoscope corresponds to a probe that is inserted into the body of a subject. Moreover, in the endoscope, an insertion portion corresponds to a movable range. Furthermore, in the endoscope, a field of view to be a subject of observation corresponds to a target scan region.

That is, in a medical diagnostic-imaging apparatus, such as IVUS, OCT, and an endoscope, a processing circuitry acquires three-dimensional medical image data (for example, CT image data) in which a subject is imaged. Moreover, the processing circuitry extracts a movable range of a probe based on a structure of the subject shown in the three-dimensional medical image data. Furthermore, the processing circuitry sets a target scan region to be a subject of scanning by the probe based on the extracted movable range. Accordingly, also in a medical diagnostic-imaging apparatus, such as IVUS, OCT, and an endoscope, a desired scan region can be set easily.

Automatic Extraction of Structure of Subject

For example, the processing circuitry 160 can extract a structure of a subject automatically.

For example, the processing circuitry 160 serving as the extracting unit extracts a structure of a subject based on a type of a probe. For example, the storage circuitry 150 stores relation information in which a type of probe and a structure of a subject are associated with each other. The type of probe is information indicating, for example, a TEE probe, an enteral probe, a transvaginal probe, or the like. Moreover, the structure of a subject is information indicating, for example, an interior wall of esophagus, an interior wall of an intestine, an interior wall of a vagina, or the like. That is, the relation information stores that a subject to extraction is "interior wall of esophagus" if the type of probe is "TEE probe". Furthermore, the relation information stores that a subject to extraction is "interior wall of intestine" if the type of probe is "enteral probe". Furthermore, the relation information stores that a subject to extraction is "interior wall of vagina" if the type of probe is "transvaginal probe". Moreover, the relation information stores characteristic information to extract various kinds of subjects of extraction by segmentation or pattern matching.

The processing circuitry 160 then automatically extracts a structure of a subject corresponding to the type of probe based on the relation information. For example, when the operator specifies "TEE probe" as the type of probe, the processing circuitry 160 refers to the relation information and identifies a subject to extraction, "interior wall of esophagus" corresponding to the type of probe, "TEE probe". The processing circuitry 160 then extracts an interior wall of the esophagus from three-dimensional medical image data by using characteristic information of an interior wall of esophagus.

The type of probe can also be identified by automatically recognizing product information, and the like from a probe connected to the ultrasonic diagnostic apparatus 1. For example, the processing circuitry 160 acquires product information from the probe connected to the ultrasonic diagnostic apparatus 1. Subsequently, the processing circuitry 160 extracts the type of probe from the acquired product information. The processing circuitry 160 then identifies the subject to extraction, "interior wall of esophagus" from the relation information based on the extracted type of probe.

Automatic Setting of Target Scan Region

For example, the processing circuitry 160 can set a target scan region automatically.

For example, the processing circuitry 160 serving as the setting unit sets a target scan region based on the type of probe. For example, the storage circuitry 150 stores the relation information in which a type of probe and a typical target scan region are associated with each other. The type of probe is information indicating, for example, a TEE probe, an enteral probe, a transvaginal probe, or the like. Moreover, the typical target scan region is information indicating a target scan region that is typically set according to a type of probe. For example, the typical target scan region is information including a typical position on a core line in a lumen region, a typical scanning direction from the position, and a typical scan range (lateral direction) based on the scanning direction as a center, and a typical depth from the position.

The processing circuitry 160 automatically extracts a typical target scan region corresponding to a type of probe based on the relation information. For example, when the operator specifies the type of probe, "TEE probe", the processing circuitry 160 refers to the relation information, and identifies information of a typical target scan region corresponding to the type of probe, "TEE probe", to set the typical target scan region. The type of probe can be identified by automatically recognizing product information and the like from a probe connected to the ultrasonic diagnostic apparatus 1.

A term "processor" used in the above explanation signifies, for example, a circuit such as a central processing unit (CPU), a graphical processing unit (GPU), an application specific integrated circuit (ASIC), a programmable logic device (for example, a simple programmable logic device (SPLD), and a complex programmable logic device (CPLD)), and a field programmable gate array (FPGA). The processor reads and executes a program stored in the storage circuitry 150, and thereby implements a function. Instead of storing the program in the storage circuitry 150, the program can be directly installed in a circuitry of the processor. In this case, the processor reads and executes the program installed in the circuitry of the processor to implement the function. Each of the processors of the embodiments is not limited to be structured as a single circuitry per processor, but can be structured by combining multiple independent processors to form a single processor to implement the function. Furthermore, more than one component in each diagram can be integrated to a single processor to implement the functions.

Moreover, the respective components of the respective devices illustrated are of functional concept, and it is not necessarily required to be configured physically as illustrated. That is, specific forms of distribution and integration of the respective devices are not limited to the ones illustrated, and all or a part thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Moreover, all or a part of the processing explained as to be performed automatically out of the respective processing explained in the above embodiments can be performed manually also, while all or a part of the processing explained as to be performed manually can be performed automatically also by a publicly-known method. In addition, the processing procedures, the control procedures, the specific names, and the information including various kinds of data and parameters indicated in the above document and the drawings can be arbitrarily modified unless otherwise specified.

Furthermore, the medical image-processing method explained in the above embodiments can be implemented by a computer, such as a personal computer and a workstation, executing a medical image-processing program prepared in advance. This medical image-processing program can be distributed through a network, such as the Internet. Moreover, this medical image-processing program can be stored in a computer-readable recording medium, such as a hard disk, a flexible disk (FD), a CD-ROM, a magneto optical disk (MO), and a digital versatile disk (DVD), and can be executed by being read by a computer from the recording medium.

Furthermore, in the above embodiments, "current" means to perform the respective processing soon after generation of each data, each time data to be processed is generated. For example, the processing of collecting current B-mode image data is a concept including a case in which an image is displayed with little delay caused due to time necessary for the respective processing, such as image processing, not limited to a case in which a time at which the subject P is imaged and a time at which the image is displayed completely coincide with each other.

According to at least one of the embodiments explained above, a desired scan region can be easily set.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image-diagnostic apparatus comprising processing circuitry configured to:
    acquire three-dimensional medical image data in which a subject is imaged,
    extract a movable range of a transesophageal probe based on a structure of the subject shown in the three-dimensional medical image data, the movable range corresponding to a body part over which the transesophageal probe is to be moved in a body of the subject,
    set a target scan region to be subject to scanning by the transesophageal probe based on the extracted movable range,
    display the target scan region in the three-dimensional medical image data,
    extract at least a lumen of an esophagus of the subject as the movable range,
    set a region in which the scanning can be performed by the transesophageal probe positioned in the lumen, based on the extracted lumen, a tiltable range of a scan region with respect to a contact surface of the transesophageal probe, and a scannable range in the scan region, the tiltable range corresponding to a limit value of a rotation angle and a limit value of a tilt range of a scan region with respect to an imaging object,
    accept a first input for changing a sectional position where the target scan region is set in the three-dimensional medical image data,
    determine whether the changed sectional position satisfies limiting conditions including the movable range, the tiltable range, and the scannable range,
    change, when the changed sectional position satisfies the limiting conditions, the sectional position in response to the first input,
    not change, when the changed sectional position does not satisfy the limiting conditions, the sectional position in response to the first input,
    accept a second input for changing the target scan region on the changed sectional position,
    determine whether the changed target scan region satisfies the limiting conditions,
    change, when the changed target scan region satisfies the limiting conditions, the target scan region in response to the second input, and
    not change, when the changed target scan region does not satisfy the limiting conditions, the target scan region in response to the second input.

2. The medical image-diagnostic apparatus according to claim 1, wherein the processing circuitry extracts a structure of the subject based on a type of the transesophageal probe.

3. The medical image-diagnostic apparatus according to claim 1, wherein the processing circuitry sets the target scan region based on a type of the transesophageal probe.

4. The medical image-diagnostic apparatus according to claim 1, wherein
    the processing circuitry sets the target scan region such that a shallowest part of the target scan region is included in the movable range.

5. The medical image-diagnostic apparatus according to claim 1, wherein
    the processing circuitry further performs positioning of a sectional image collected by the scanning and the three-dimensional medical image data, and
        outputs guiding information to bring a scan region corresponding to the sectional image move to a target scan region based on a difference between the scan region corresponding to the sectional image subjected to the positioning and the target scan region set in the three-dimensional medical image data subjected to the positioning.

6. The medical image-diagnostic apparatus according to claim 5, wherein
    the processing circuitry sets a plurality of the target scan regions, and
        outputs the guiding information based on a difference between a target scan region that is selected from among the set target scan regions and a scan region corresponding to the sectional image.

7. The medical image-diagnostic apparatus according to claim 5, wherein the processing circuitry
    sets a plurality of the target scan regions, and
    outputs a plurality of pieces of guiding information to bring a scan region of the transesophageal probe move to each of the target scan regions at a time based on a difference between each of the set target scan regions and a scan region corresponding to the sectional image.

8. The medical image-diagnostic apparatus according to claim 5, wherein the processing circuitry
    acquires a plurality of pieces of the three-dimensional medical image data that are obtained by imaging a region including a heart of the subject at a plurality of cardiac phases different from each other, and uses, when the plurality of pieces of the three-dimensional medical image data include three-dimensional medical image data in which the target scan region has been set and three-dimensional medical image data in which a target scan region has not been set, information of the target scan region already been set as an initial position to set the target scan region in the three-dimensional medical image data in which a target scan region has not been set.

9. The medical image-diagnostic apparatus according to claim 8, wherein the processing circuitry performs positioning of three-dimensional medical image data of a selected cardiac phase out of the cardiac phases and the sectional image, and outputs the guiding information based on a difference between the target scan region at the selected cardiac phase out of the cardiac phases and a scan region corresponding to the sectional image.

10. The medical image-diagnostic apparatus according to claim 5, wherein when the scanning is performed by a two-dimensional array probe or a mechanical 4D (mecha4D) probe, the processing circuitry brings a direction of the scan region move to a direction of the target scan region by controlling an electronic scanning of the two-dimensional array probe or a swinging direction of the mecha4D probe.

11. A medical image-processing apparatus comprising processing circuitry configured to:

acquire three-dimensional medical image data in which a subject is imaged, extract a movable range of a transesophageal probe based on a structure of the subject shown in the three-dimensional medical image data, the movable range corresponding to a body part over which the transesophageal probe is to be moved in a body of the subject, set a target scan region to be subject to scanning by the transesophageal probe based on the extracted movable range, display the target scan region in the three-dimensional medical image data, extract at least a lumen of an esophagus of the subject as the movable range, and set a region in which the scanning can be performed by the transesophageal probe positioned in the lumen, based on the extracted lumen, a tiltable range of a scan region with respect to a contact surface of the transesophageal probe, and a scannable range in the scan region, the tiltable range corresponding to a limit value of a rotation angle and a limit value of a tilt range of a scan region with respect to an imaging object, accept a first input for changing a sectional position where the target scan region is set in the three-dimensional medical image data, determine whether the changed sectional position satisfies limiting conditions including the movable range, the tiltable range, and the scannable range, change, when the changed sectional position satisfies the limiting conditions, the sectional position in response to the first input, not change, when the changed sectional position does not satisfy the limiting conditions, the sectional position in response to the first input, accept a second input for changing the target scan region on the changed sectional position, determine whether the changed target scan region satisfies the limiting conditions, change, when the changed target scan region satisfies the limiting conditions, the target scan region in response to the second input, and not change, when the changed target scan region does not satisfy the limiting conditions, the target scan region in response to the second input.

12. A medical image-diagnostic apparatus comprising processing circuitry configured to:

acquire three-dimensional medical image data in which a subject is imaged, extract a movable range of a transesophageal probe based on a structure of the subject shown in the three-dimensional medical image data, the movable range corresponding to a body part over which the transesophageal probe is to be moved in a body of the subject, set a target scan region to be subject to scanning by the transesophageal probe based on the extracted movable range, display the target scan region in the three-dimensional medical image data, extract at least a lumen of an esophagus of the subject as the movable range, and set a region in which the scanning can be performed by the transesophageal probe positioned in the lumen, based on the extracted lumen, a tiltable range of a scan region with respect to a contact surface of the transesophageal probe, and a scannable range in the scan region, the tiltable range corresponding to a limit value of a rotation angle and a limit value of a tilt range of a scan region with respect to an imaging object, accept a first input for changing a sectional position for display object in the three-dimensional medical image data, determine whether the changed sectional position satisfies the movable range and the tiltable range, change, when the changed sectional position satisfies the movable range and the tiltable range, the sectional position in response to the first input, not change, when the changed sectional position does not satisfy the movable range and the tiltable range, the sectional position in response to the first input, accept a second input for setting a parameter of the target scan region on the changed sectional position, the parameter including a position of a shallowest part, a scanning direction, a width in an azimuth direction, and a depth in a depth direction of the target scan region, determine whether the set parameter satisfies the scannable range, change, when the set parameter satisfies the scannable range, the parameter in response to the second input, and not change, when the set parameter does not satisfy the scannable range, the parameter in response to the second input.

13. A medical image-processing apparatus comprising processing circuitry configured to:

acquire three-dimensional medical image data in which a subject is imaged, extract a movable range of a transesophageal probe based on a structure of the subject shown in the three-dimensional medical image data, the movable range corresponding to a body part over which the transesophageal probe is to be moved in a body of the subject, set a target scan region to be subject to scanning by the transesophageal probe based on the extracted movable range, display the target scan region in the three-dimensional medical image data, extract at least a lumen of an esophagus of the subject as the movable range, and set a region in which the scanning can be performed by the transesophageal probe positioned in the lumen, based on the extracted lumen, a tiltable range of a scan region with respect to a contact surface of the transesophageal probe, and a scannable range in the scan region, the tiltable range corresponding to a limit value of a rotation angle and a limit value of a tilt range of a scan region with respect to an imaging object, accept a first input for changing a sectional position for display object in the three-dimensional medical image data, determine whether the changed sectional position satisfies the movable range and the tiltable range, change, when the changed sectional position satisfies the movable range and the tiltable range, the sectional position in response to the first input, not change, when the changed sectional position does not satisfy the movable range and the tiltable range, the sectional position in response to the first input, accept a second input for setting a parameter of the target scan region on the changed sectional position, the parameter including a position of a shallowest part, a scanning direction, a width in an azimuth direction, and a depth in a depth direction of the target scan region, determine whether the set parameter satisfies the scannable range, change, when the set parameter satisfies the scannable range, the parameter in response to the second input, and not change, when the set parameter does not satisfy the scannable range, the parameter in response to the second input.

* * * * *